(12) United States Patent
Smit

(10) Patent No.: US 9,241,963 B2
(45) Date of Patent: Jan. 26, 2016

(54) MEDICAMENT FOR TREATING MUSCLE AND SKELETAL DISEASES

(71) Applicant: Biologische Heilmittel Heel GmbH, Baden-Baden (DE)

(72) Inventor: Anna Aletta Smit, Baden-Baden (DE)

(73) Assignee: Biologische Heilmittel Heel GmbH, Baden-Baden (DE)

( * ) Notice: Subject to any disclaimer, the term of this patent is extended or adjusted under 35 U.S.C. 154(b) by 0 days.

(21) Appl. No.: 14/245,787

(22) Filed: Apr. 4, 2014

(65) Prior Publication Data

US 2015/0283189 A1 Oct. 8, 2015

(51) Int. Cl.

| A61K 36/185 | (2006.01) |
|---|---|
| A61K 36/714 | (2006.01) |
| A61K 36/28 | (2006.01) |
| A61K 36/81 | (2006.01) |
| A61K 33/06 | (2006.01) |
| A61K 33/28 | (2006.01) |
| A61K 36/30 | (2006.01) |
| A61K 36/22 | (2006.01) |
| A61K 36/66 | (2006.01) |
| A61K 33/04 | (2006.01) |
| A61K 31/7076 | (2006.01) |
| A61K 35/54 | (2015.01) |
| A61K 35/51 | (2015.01) |
| A61K 35/50 | (2015.01) |

(52) U.S. Cl.
CPC ........... *A61K 36/185* (2013.01); *A61K 31/7076* (2013.01); *A61K 33/04* (2013.01); *A61K 33/06* (2013.01); *A61K 33/28* (2013.01); *A61K 35/50* (2013.01); *A61K 35/51* (2013.01); *A61K 35/54* (2013.01); *A61K 36/22* (2013.01); *A61K 36/28* (2013.01); *A61K 36/30* (2013.01); *A61K 36/66* (2013.01); *A61K 36/714* (2013.01); *A61K 36/81* (2013.01)

(58) Field of Classification Search
IPC .................................................... A61K 36/00
See application file for complete search history.

(56) References Cited

U.S. PATENT DOCUMENTS

| 2007/0071840 A1* | 3/2007 | Dhanaraj et al. ............. 424/764 |
| 2011/0250259 A1* | 10/2011 | Buckman ..................... 424/450 |

OTHER PUBLICATIONS

Altman et al., "Development of Criteria for the Classification and Reporting of Osteoarthritis," *Arthritis Rheum* 29: 1039-1049 (1986).
Basini, et al., "Sanguinarine Inhibits VEGF—Induced AKT Phosphorylation," Ann N Y Acad Sci 1095: 371-6 (2007).
Basini, et al., "Sanguinarine inhibits VEGF—induced angiogenesis in a fibrin gel matrix," Biofactors 29(1): 11-18 (2007).
Arroll et al., "Corticosteroid injections for osteoarthritis of the knee: meta-analysis," BMJ, pp. 1-5 (2004).
Conforti, et al., "Experimental Studies on the Anti-Inflammatory Activity of a Homeopathic Preparation," Biomed Therapy 15: 28-31 (1997).
Felson, et al., "The Prevalence of Knee Osteoarthritis in the Elderly," Arthritis Rheum 30(8): 914-918 (1987).
Fries, et al., "Measurement of Patient Outcome in Arthritis," Arthritis Rheum 23: 137-145 (1980).
Heine, "Induction of the Immunological Bystander Reaction by Plant Extracts," Biomed Ther., vol. XVI, No. 3, pp. 224-226 (1998).
Heine, "The anti-inflammatory Mechanism of Action of a Antihomotoxikum Compositum," Naturopathic Arztezeitschrift, 43: 96-104 (2002) [Eng. Translation included].
Jäggi et al., "Dual inhibition of 5-lipoxygenase/cyclooxygenase by a reconstituted homeopathic remedy; possible explanation for clinical efficacy and favourable gastrointestinal tolerability," Inflamm. Res. 53(4): 150-7 (2004).
Kirchner, et al., "A double-blind randomized controlled trial comparing alternate forms of high molecular weight hyaluronan for the treatment of osteoarthritis of the knee," OsteoArthritis Cartilage 14(2): 154-62 (2006).
Laine, "GI Risk and Risk Factors of NSAIDs," J Cardiovasc Pharmacol 47 Suppl 1, 60-66 (2006).
Lussignoli, et al., "Effect of Traumel S®, a homeopathic formulation, on blood-induced inflammation in rats," Complement Ther Med 7: 225-230 (1999).
Porozov, et al., "Inhibition of IL-1β and TNF-α Secretion from Resting and Activated Human Immunocytes by the Homeopathic Medication Traumeel® S," Clin Dev Immunol 2: 143-9 (2004).
Rutjes, et al., "Viscosupplemention for Osteoarthritis of the Knee," Ann Intern Med 157(3): 180-191 (2012).
Schmolz, Transforming Growth Factor beta (TGF-B): Eine neue Regelstrecke fur antiphlogistische Therapien? Biol Med 29(1): 31-34 (2000).
Schmolz et al., "Homoopathische Substanzen aus der antihomotoxischen Medizin modulieren die Synthese von TGF-B, in menschlichen Vollblutkulturen," Biol Med 30(2): 61-65 (2001).
Schneider, et al., "The role of a homoeopathic preparation compared with conventional therapy in the treatment of injuries: An observational cohort study," Complement Ther. Med. 16: pp. 22-27 (2008).

(Continued)

Primary Examiner — Rosanne Kosson
(74) Attorney, Agent, or Firm — Foley & Lardner LLP

(57) ABSTRACT

The present invention concerns the field of therapy of muscle, joint and/or skeletal diseases. In particular, the invention relates to a composition comprising a first solution comprising preparations of *Aconitum napellus, Arnica montana, radix, Bellis perennis, Belladonna, Calendula officinalis, Chamomilla, Echinacea, Echinacea purpurea, Hamamelis virginiana, Hepar sulfuris calcareum, Hypericum perforatum*, Mercuris solubilis, *Millefolium*, and *Symphytum officinale*, and a second solution comprising preparations of *Arnica montana, radix, Dulcamara, Rhus toxicodendron, Sanguinaria Canadensis*, and Sulphur. Further provided is a method of treating and/or preventing the progression of a disease comprising administering to a subject in need of a treatment a therapeutically effective amount of the said composition or said first and said second solution. The invention also contemplates a kit comprising said first and said second solution.

21 Claims, No Drawings

(56) References Cited

OTHER PUBLICATIONS

St. Laurent, G., et al., "Deep Sequencing Transcriptome Analysis of Traumeel Therapeutic Action in Wound Healing," Annals of the Rheumatic Diseases; vol. 72: Suppl 3 (2013) [Abstract].

Stancikova, et al., "Effects of Zeek Comp. on Experimental Osteoarthritis in Rabbit Knee," Rheumatologia 13(3): 101-108 (1999).

Tunon, et al., "Evaluation of anti-inflammatory activity of some Swedish medicinal plants. Inhibition of prostaglandin biosynthesis and PAF-induced exocytosis," J Enteropharmacol 48: 61-76 (1995).

Weh, et al., "Incubation in Preparations as a Means of Influencing Cartiliage Mechanics: A Mechanical Study," Biol Ther 8(4): 91-93 (1990).

* cited by examiner

MEDICAMENT FOR TREATING MUSCLE AND SKELETAL DISEASES

INTRODUCTION

The present invention concerns the field of therapy of muscle, joint and/or skeletal diseases. In particular, the invention relates to a composition comprising a first solution comprising preparations of *Aconitum napellus, Arnica montana, radix, Bellis perennis, Belladonna, Calendula officinalis, Chamomilla, Echinacea, Echinacea purpurea, Hamamelis virginiana, Hepar sulfuris calcareum, Hypericum perforatum, Mercuris solubilis, Millefolium*, and *Symphytum officinale*, and a second solution comprising preparations of *Arnica montana, radix, Dulcamara, Rhus toxicodendron, Sanguinaria Canadensis*, and Sulphur. Further provided is a method of treating and/or preventing the progression of a disease comprising administering to a subject in need of a treatment a therapeutically effective amount of the said composition or said first and said second solution. The invention also contemplates a kit comprising said first and said second solution.

BACKGROUND OF THE INVENTION

Inflammatory or degenerative condition of the musculoskeletal system, such as arthrosis, osteoarthritis, rheumatic joint disease, joint stiffness, pain in connection with muscles, joints and surrounding tissues or the skeleton, and swelling in connection with muscles or joints and surrounding tissues, are painful and frequent medical conditions, in particular, in the elderly.

In particular, osteoarthritis (OA), the most common form of joint disease, affects as much as 80% of the general population. The degenerative joint changes that characterize this disorder are radiologically detectable and include subchondral bony sclerosis, synovitis, loss of articular cartilage, and osteophytes formed by proliferation of bone and cartilage in the joint Altman 1986, Arthritis Rheum 29: 1039-1049). In about 60% of sufferers these changes are accompanied by symptoms that include erythema, swelling and joint pain that often result in reports of morning stiffness, limitations in range of motion and restrictions in the activities of daily living (Fries 1980, Arthritis Rheum 23: 137-145).

The Framingham Osteoarthritis study demonstrated that radiographic evidence of OA increased with age, from 27% in patients younger than age 70, to 44% in patients age 80 or older. There was a slightly higher prevalence of radiographic changes of OA in women than in men (34% versus 31%); however, there was a significantly higher proportion of women with symptomatic disease (11% of all women versus 7% of all men; p=0.003) (Felson 1987, Arthritis Rhem 30(8): 914-918).

Pharmacological treatments for OA include analgesics, non-steroidal anti-inflammatory drugs (NSAIDs), intra-articular (IA) injections of steroids and IA injections of viscosupplementation in the form of hyaluronic acid (HA) (Kirchner 2006. Osteoarthritis Catilage 14(2): 154-62). Several retrospective analyses have concluded that non-selective NSAIDs pose an increased risk of gastrointestinal adverse events (AEs) (see, e.g., Laine 2006, J Cardiovasc Pharmacol 47 Suppl 1, 60-66) In general, these analyses have looked at patients undergoing long-term chronic therapy often with underlying inflammatory diseases such as OA. Intra-articular injection of steroid is also a common treatment for osteoarthritis of the knee. However, clinical evidence suggests that the benefit is short-lived, usually one to four weeks (Bruce 2004, BMJ, doi:10.1136/bmj.38039.573970.7C). Additionally, concern has been expressed that long-term treatment could promote joint destruction and tissue atrophy.

The data from clinical trials of viscosupplement products available in the public domain utilized heterogeneous methodologies and endpoints, and comparisons are therefore relatively difficult to interpret. These products appear to provide, at best, consistently moderate symptom improvement of OA knee pain despite the fact that viscosupplementation is universally used at a very significant cost. Improvements are often directional, and even when statistically significant, may not exhibit clinical endpoint effect sizes consistent with clinically relevant outcomes. It has, in fact, been concluded in a systematic review of the literature that IA HA has not been proven clinically effective and may be associated with a greater risk of AEs (Rutjes 2012, Ann Intern Med 157(3): 180-191).

In light of the increasing prevalence of OA in a large and aging "baby-boomer" population in the United States, there is a clear public health need for new OA treatment approaches that do not present potentially harmful outcomes.

Two homeopathic drugs have been suggested for therapy of conditions of the skeletal and muscle system.

Traumeel® Injection Solution (Traumeel® injection) is a marketed anti-inflammatory, anti-edematous, anti-exudative combination formulation of 12 botanical substances and 2 mineral substances. Traumeel® injection is officially classified as a homeopathic combination medication (Homeopatic Pharmacopeias Europe (Ph Eur) and US (HPUS)). Botanical ingredients are *Arnica montana radix* (mountain arnica), *Calendula officinalis* (marigold), *Hamamelis virginiana* (witch hazel), *Millefolium* (milfoil), *Belladonna* (deadly nightshade), *Aconitum napellus* (monkshood), *Chamomilla* (chamomile), *Symphytum officinale* (comfrey), *Bellis perennis* (daisy), *Echinacea angustifolia* (narrowleafed cone flower). *Echinacea purpurea* (purple cone flower), and *Hypericum perforatum* (St. John's wort). The mineral ingredients are *Hepar sulphuris calcareum* (calcium sulfide) and Mercurius solubilis Hahnemanni (Dimercuros ammonium nitrate). The ingredients are decimal attenuations of different potencies as per the Homeopathic Pharmacopoeia of the United States (HPUS).

Traumeel® is a multicomponent and multitargeting complex homeopathic medication. The exact mechanism of action of Traumeel® has not been fully elucidated. However, in vitro and animal studies point to a multi-targeted mechanism of action.

Various cellular and biochemical pathways appear to be modulated by the ingredients of Traumeel®, which act synergistically on the different phases of the inflammatory response (Lussignoli 1999, Complement Ther Med 7: 225-230). However, Traumeel® injection does not inhibit the arachidonic acid pathway of prostaglandin synthesis. Traumeel® appears to reduce acute local inflammation without affecting the normal defensive and homeostatic functions of granulocytes or platelets, and to regulate the orchestration of the overall acute local inflammatory process instead of interacting with a specific cell type or biochemical mechanism (Conforti 1997, Biomed ther 15: 28-31). Preclinical studies suggest Traumeel® inhibits the secretion of pro-inflammatory mediators, and regulates lymphocytes and their messengers (e.g. transforming growth factor-beta, tumour necrosis factor-alpha and interleukin-1 (Porozov 2004, Clin Dev Immunol 2: 143-9; Heine 2002, Ärztezeitschrift für Naturheilverfahren 43: 96-104; Heine 1998, Biomed Ther XVI: 224-6). Traumeel® also seems to act by accelerating the healing process rather than blocking edema development from the start, with beneficial effects on tissue repair and wound healing (Lussignoli 1990, loc. cit., Conforti 1997, loc. cit., Heine 1998, loc. cit., Heine 2002, loc. cit., Schneider 2008, Complement Ther Med 16-22-7). Lastly in recent genomic studies, Traumeel® has been seen to have beneficial effects on the inflammatory process in a wound healing model (St. Laurent, G., M. Tackett, T. McCaffrey, P. Kapranov. DEEP SEQUENCING TRANSCRIPTOME ANALYSIS OF TRAUMEEL THERAPEUTIC ACTION IN WOUND HEALING. Annals of the Rheumatic Diseases; Vol 72: Suppl 3 [Abstract THU0016] (2013)).

Zeel® injection solution is officially classified as a homeopathic combination medication (Homeopatic Pharmacopeias Europe (Ph Eur) and US (HPUS)). Botanical or animal ingredients are *Arnica montana, radix, Cartilago suis* (porcine cartilage), Coenzyme A, *Solanum dulcamara* (bittersweet), *Embryo totalis suis* (porcine embryo), *Funiculus umbilicalis suis* (porcine umbilical cord), *Placenta suis* (porcine placenta), *Rhus toxicodendron* (poison oak), *Sanguinaria Canadensis* (blood root), *Symphytum officinale* cornfrey). The mineral ingredients are *Natrum oxalaceticum* (di-sodium oxaloacetate), *Nadidum* (beta-NAD), a-Lipoicum acidum (thioctic acid), and Sulphur (sulfur). The ingredients are decimal attenuations of different potencies as per the Homeopathic Pharmacopoeia of the United States (HPUS).

Zeel® has been shown to modulate chronic inflammatory processes by inhibiting the production of leukotriene B4 by 5-lipoxygenase and Traumeel® the synthesis of prostaglandin E2 by cyclooxygenase (COX)-1 and COX-2 enzymes (Jäggi 2004, Inflamm Res 53(4): 150-7; Tunon 1995, J Enteropharmacol 48: 61-76). Zeel® injections have also demonstrated several different roles in preserving cartilage. It appears to act as an anti-angiogenic agent by preventing vascularisation of cartilage and endochondrium, and stimulates the release of transforming growth factor-beta, which is involved in immunomodulation and tissue remodeling (Basini 2007, Biofactors 29(1): 11-18; Basini 2007, Ann N Y Acad Sci 1095: 371-6; Schmolz 2000, Biol Med 29(1): 31-34; Schmolz 2001, Biol Med 30(2): 61-65). Additionally, Zeel® significantly decreases the severity of cartilage damage, and improves the mechanical properties of osteoarthritic cartilage by increasing its elasticity (Stancikova 1999, Rheumatologia 13(3): 101-108; Weh 1990, Biol Ther 8(4): 91-93).

However, improved therapies for OA and other inflammatory or degenerative conditions of the musculoskeletal system are not yet available but still highly desired.

SUMMARY OF THE INVENTION

The present invention relates to a composition comprising
(i) a first solution comprising preparations of *Aconitum napellus, Arnica montana, radix, Bellis perennis, Belladonna, Calendula officinalis, Chamomilla* (Matricaria recutita), *Echinacea, Echinacea purpurea, Hamamelis virginiana, Hepar sulfuris calcareum, Hypericum perforatum, Mercuris solubilis, Millefolium,* and *Symphytum officinale,* and
(ii) a second solution comprising preparations of *Arnica montana, radix, Dulcamara, Rhus toxicodendron, Sanguinaria Canadensis,* and Sulphur.

In one aspect of the composition of the invention, said preparations are applied in the first solution of the composition in potencies according to the homeopathic pharmacopeia as follows: *Aconitum napellus* 2×, *Arnica montana, radix* 2×, *Bellis perennis* 2×, *Belladonna* 2×, *Calendula officinalis* 2×, *Chamomilla* 3×, *Echinacea* 2×, *Echinacea purpurea* 2×, *Hamamelis virginiana* 1×, *Hepar sulfuris calcareum* 6×, *Hypericum perforatum* 2×, *Mercuris solubilis* 6×, *Millefolium* 3×, and *Symphytum officinale* 6×.

In another aspect of the composition of the invention, the preparations are present in the first solution of the composition in an amount per 2.2 ml of about: *Aconitum napellus* 1.32 μl, *Arnica montana, radix* 2.2 μl, *Bellis perennis* 1.1 μl, *Belladonna* 2.2 μl, *Calendula officinalis* 2.2 μl, *Chamomilla* 2.2 μl, *Echinacea* 0.55 *Echinacea purpurea* 0.55 μl, *Hamamelis virginiana* 0.22 μl, *Hepar sulfuris calcareum* 2.2 μl, *Hypericum perforatum* 0.66 μl, Mercuris solubilis 1.1 μl, *Millefolium* 2.2 μl, and *Symphytum officinale* 2.2 μl.

In an aspect of the composition of the invention, said preparations are applied in the second solution of the composition in potencies according to the homeopathic pharmacopeia as follows: *Arnica montana, radix* 4×, *Dulcamara* 4×, *Rhus toxicodendron* 4×, *Sanguinaria Canadensis* 4×, and Sulphur 10×.

In another aspect of the composition of the invention, the preparations are present in the second solution of the composition in an amount per 2 g of about: *Arnica montana, radix* 2 mg, *Dulcamara* 1 mg, *Rhus toxicodendron* 10 mg, *Sanguinaria Canadensis* 1 mg, and Sulphur 3 mg.

In yet an aspect of the composition of the invention, said second solution comprises preparations of a-Lipoicum acidum, *Arnica montana, radix, Cartilago suis,* Coenzyme A, *Dulcamara, Embryo totalis suis, Funiculus umbilicalis suis, Nadidum, Natrum oxalaceticum, Placenta suis, Rhus toxicodendron, Sanguinaria Canadensis,* Sulphur, *Symphytum officinale.*

In a further aspect of the composition of the invention, said preparations are applied in the second solution of the composition in potencies according to the homeopathic pharmacopeia as follows: a-Lipoicum acidum 8×, *Arnica montana, radix* 4×, *Cartilago suis* 6×, Coenzyme A 8×, *Dulcamara* 3×, *Embryo totalis suis* 6×, *Funiculus umbilicalis suis* 6×, *Nadidum* 8×, *Natrum oxalaceticum* 8×, *Placenta suis* 6×, *Rhus toxicodendron* 2×, *Sanguinaria canadensis* 4×, Sulphur 6×, *Symphytum officinale* 6×.

In another aspect of the composition of the invention, the preparations are present in the second solution of the composition in an amount per 2.0 ml of about: a-Lipoicum acidum 2.0 μl, *Arnica montana, radix* 200.0 μl, *Cartilago suis* 2.0 μl, Coenzyme A 2.0 μl, *Dulcamara* 10.0 μl, *Embryo totalis suis* 2.0 μl, *Funiculus umbilicalis suis* 2.0 μl, *Nadidum* 2.0 *Natrum oxalaceticum* 2.0 μl, *Placenta suis* 2.0 *Rhus toxicodendron* 10.0 μl, *Sanguinaria canadensis* 3.0 μl, Sulphur 3.6 μl, *Symphytum officinale* 10.0 μl.

In an aspect of the composition of the invention, said composition further comprises at least one pharmaceutically acceptable diluent and/or carrier.

In another aspect of the composition of the said composition is an injection solution.

The present invention further relates to a method of treating and/or preventing the progression of a disease comprising administering to a subject in need of a treatment a therapeutically effective amount of the composition of the invention.

In an aspect of the method of the invention, said disease is an inflammatory or degenerative condition of the musculoskeletal system.

In another aspect of the method of the invention, said inflammatory or degenerative condition of the musculoskeletal system is a disease or condition selected from the group consisting of arthrosis, osteoarthritis, rheumatic joint disease, joint stiffness, pain in connection with muscles joints and surrounding tissues or skeleton, and swelling in connection with muscles, joints and the surrounding tissues In yet an aspect of the method of the invention, said composition is administered parenteral and, in particular, intradermal, intra-muscular, intra- or peri-articular or intravenously.

The present invention further relates to a kit comprising a first composition and a second composition, said first solution comprising preparations of *Aconitum napellus, Arnica montana, radix, Bellis perennis, Belladonna, Calendula officinalis, Chamomilla, Echinacea, Echinacea purpurea, Hamamelis virginiana, Hepar sulfuris calcareum. Hypericum perforatum, Mercuris solubilis, Millefolium*, and *Symphytum officinale*, and said second solution comprising preparations of *Arnica montana, radix, Dulcamara, Rhus toxicodendron, Sanguinaria Canadensis*, and Sulphur.

In an aspect of the kit of the invention, said preparations are applied in the first solution in potencies according to the homeopathic pharmacopeia as follows: *Aconitum napellus* 2×. *Arnica montana, radix* 2×, *Bellis perennis* 2×, *Belladonna* 2×, *Calendula officinalis* 2×, *Chamomilla* 3×, *Echinacea* 2×, *Echinacea purpurea* 2×, *Hamamelis virginiana* 1×, *Hepar sulfuris calcareum* 6×, *Hypericum perforatum* 2×, *Mercuris solubilis* 6×, *Millefolium* 3×, and *Symphytum officinale* 6×.

In another aspect of the kit of the invention, the preparations are present in the first solution in an amount per 2.2 ml of about: *Aconitum napellus* 1.32 µl, *Arnica montana, radix* 2.2 µl, *Bellis perennis* 1.1 µl, *Belladonna* 2.2 µl, *Calendula officinalis* 2.2 µl, *Chamomilla* 2.2 µl, *Echinacea* 0.55 µl, *Echinacea purpurea* 0.55 µl, *Hamamelis virginiana* 0.22 µl, *Hepar sulfuris* calcareum 2.2 µl, *Hypericum perforatum* 0.66 µl, Mercuris solubilis 1.1 µl, *Millefolium* 2.2 µl, and *Symphytum officinale* 2.2 µl.

In an aspect of the kit of the invention, said preparations are applied in the second solution of the composition in potencies according to the homeopathic pharmacopeia as follows: *Arnica montana, radix* 4×, *Dulcamara* 4×, *Rhus toxicodendron* 4×, *Sanguinaria Canadensis* 4×, and Sulphur 10×.

In another aspect of the kit of the invention, the preparations are present in the second solution of the composition in an amount per 2 g of about: *Arnica montana, radix* 2 mg, *Dulcamara* 1 mg, *Rhus toxicodendron* 10 mg. *Sanguinaria Canadensis* 1 mg, and Sulphur 3 mg.

In yet an aspect of the kit of the invention, said second solution comprises preparations of a-Lipoicum acidum, *Arnica montana, radix, Cartilago suis*, Coenzyme A, *Dulcamara, Embryo totalis suis, Funiculus umbilicalis suis, Nadidum, Natrum oxalaceticum, Placenta suis, Rhus toxicodendron, Sanguinaria Canadensis*, Sulphur, *Symphytum officinale*.

In yet an aspect of the kit of the invention, said preparations are applied in the second solution in potencies according to the homeopathic pharmacopeia as follows: a-Lipoicum acidum 8×, *Arnica montana, radix* 4×, *Cartilago suis* 6×, Coenzyme A 8×, *Dulcamara* 3×, *Embryo totalis* suis 6×, *Funiculus umbilicalis suis* 6×, Nadidum 8×, Natrum oxalaceticum 8×, *Placenta suis* 6×, *Rhus toxicodendron* 2×, *Sanguinaria canadensis* 4×, Sulphur 6×, *Symphytum officinale* 6×.

In an aspect of the kit of the invention, the preparations are present in the second solution in an amount per 2.0 ml of about: a-Lipoicum acidum 2.0 µl, *Arnica montana, radix* 200.0 µl, *Cartilago suis* 2.0 µl. Coenzyme A 2.0 *Dulcamara* 10.0 µl, *Embryo totalis suis* 2.0 µl, *Funiculus umbilicalis suis* 2.0 µl. Nadidum 2.0 µl. Natrum oxalaceticum 2.0 µl, *Placenta suis* 2.0 µl, *Rhus toxicodendron* 10.0 *Sanguinaria canadensis* 3.0 µl, Sulphur 3.6 µl, *Symphytum officinale* 10.0 µl.

The present invention further relates to a method of treating and/or preventing the progression of a disease comprising administering to a subject in need of a treatment a therapeutically effective amount of a first and a second solution, said first solution comprising preparations of *Aconitum napellus, Arnica montana, radix, Bellis perennis, Belladonna, Calendula officinalis, Chamomilla, Echinacea, Echinacea purpurea, Hamamelis virginiana, Hepar sulfuris caleareum, Hypericum perforatum, Mercuris solubilis, Millefolium*, and *Symphytum officinale*, and said second solution comprising preparations of *Arnica montana, radix, Dulcamara, Rhus toxicodendron, Sanguinaria Canadensis*, and Sulphur.

In an aspect of the said method of the invention, said preparations are applied in the first solution in potencies according to the homeopathic pharmacopeia as follows: *Aconitum napellus* 2×, *Arnica montana, radix* 2×. *Bellis perennis* 2×, *Belladonna* 2×, *Calendula officinalis* 2×, *Chamomilla* 3×, *Echinacea* 2×, *Echinacea purpurea* 2×, *Hamamelis virginiana* 1×, *Hepar sulfuris calcareum* 6×, *Hypericum perforatum* 2×, *Mercuris solubilis* 6×, *Millefolium* 3×, and *Symphytum officinale* 6×.

In yet an aspect of the said method of the invention, the preparations are present in the first solution in an amount per 2.2 ml of about: *Aconitum napellus* 1.32 µl, *Arnica montana, radix* 2.2 µl *Bellis perennis* 1.1 *Belladonna* 2.2 µl *Calendula officinalis* 2 µl. *Chamomilla* 2.2 µl, *Echinacea* 0.55 µl, *Echinacea purpurea* 0.55 µl, *Hamamelis virginiana* 0.22 *Hepar sulfuris calcareum* 2.2 *Hypericum perforatum* 0.66 µl, Mercuris solubilis 1.1 µl, *Millefolium* 2.2 µl, and *Symphytum officinale* 2.2 µl.

In an aspect of the method of the invention, said preparations are applied in the second solution of the composition in potencies according to the homeopathic pharmacopeia as follows: *Arnica montana, radix* 4×, *Dulcamara* 4×, *Rhus toxicodendron* 4×, *Sanguinaria Canadensis* 4×, and Sulphur 10×.

In another aspect of the method of the invention, the preparations are present in the second solution of the composition in an amount per 2 g of about: *Arnica montana, radix* 2 mg, *Dulcamara* 1 mg, *Rhus toxicodendron* 10 mg, *Sanguinaria Canadensis* 1 mg, and Sulphur 3 mg.

In yet an aspect of the method of the invention, said second solution comprises preparations of a-Lipoicum acidum, *Arnica montana, radix, Cartilago suis*, Coenzyme A, *Dulcamara, Embryo totalis suis, Funiculus umbilicalis suis, Nadidum, Natrum oxalaceticum, Placenta suis, Rhus toxicodendron, Sanguinaria Canadensis*, Sulphur, *Symphytum officinale*.

In a further aspect of the said method of the invention, said preparations are applied in the second solution in potencies according to the homeopathic pharmacopeia as follows: a-Lipoicum acidum 8×, *Arnica montana, radix* 4×, *Cartilago suis* 6×. Coenzyme A 8×, *Dulcamara* 3×, *Embryo totalis suis* 6×, *Funiculus umbilicalis suis* 6×. Nadidum 8×, Natrum oxalaceticum 8×, *Placenta suis* 6×, *Rhus toxicodendron* 2×, *Sanguinaria canadensis* 4×, Sulphur 6×, *Symphytum officinale* 6×.

In an aspect of the said method of the invention, the preparations are present in the second solution in an amount per 2.0 ml of about: a-Lipoicum acidum 2.0 *Arnica montana, radix* 200.0 *Cartilago suis* 2.0 Coenzyme A 2.0 *Dulcamara* 10.0 *Embryo totalis suis* 2.0 *Funiculus umbilicalis suis* 2.0 Nadidum 2.0 Natrum oxalaceticum 2.0 *Placenta suis* 2.0 *Rhus toxicodendron* 10.0 *Sanguinaria canadensis* 3.0 Sulphur 3.6 *Symphytum officinale* 10.0 µl.

In yet an aspect of the said method of the invention, said disease is an inflammatory or degenerative condition of the musculoskeletal system.

In another aspect of the said method of the invention, said inflammatory or degenerative condition of the musculoskeletal system is a disease or condition selected from the group consisting of: arthrosis, osteoarthritis, rheumatic joint disease, joint stiffness, pain in connection with muscles or skeleton, and swelling in connection with muscles or skeleton.

In a further aspect of the said method of the present invention, said compositions are administered parenteral and, in particular intra-dermal, intra-muscular, intra- or peri-articular or intra-venously.

DETAILED DESCRIPTION

The present invention relates to a composition comprising
(i) a first solution comprising preparations of *Aconitum napellus, Arnica montana, radix, Bellis perennis, Belladonna, Calendula officinalis, Chamomilla, Echinacea, Echinacea purpurea, Hamamelis virginiana, Hepar sulfuris calcareum, Hypericum perforatum, Mercuris solubilis, Millefolium,* and *Symphytum officinale*, and
(ii) a second solution comprising preparations of *Arnica montana, radix, Dulcamara, Rhus toxicodendron, Sanguinaria Canadensis,* and Sulphur.

The term "composition as used herein refers to a mixture of preparations from, inter alia, biological sources and non-biological sources which are provided as a first and a second solution as defined elsewhere herein. In an aspect, the said composition can further comprise other ingredients or diluents. Such further ingredients can be stabilizing agents, wetting agents, pharmaceutical carriers, additional pharmaceutically active agents, release controlling agents, adjuvants and the like and the like. In an aspect, diluents encompass distilled water, sodium chloride solution, alcohols, physiological saline solutions, buffers, such as phosphate buffered saline solutions, Ringer's solutions, dextrose solution, and Hank's solution, syrup, oil, water, emulsions, various types of wetting agents, and the like. In yet an aspect, it is envisaged in accordance with the present invention that a composition further comprises at least one pharmaceutically acceptable carrier and/or diluent. The carrier(s) must be acceptable in the sense of being compatible with the other ingredients of the formulation and being not deleterious to the recipient thereof. Suitable carriers comprise those mentioned above and others well known in the art, see, e.g., Remington's Pharmaceutical Sciences, Mack Publishing Company, Easton, Pa. The pharmaceutically acceptable diluent is selected so as not to affect the biological activity of the combination.

The composition shall be adapted for use in treating and/or preventing the diseases or disorders referred to herein. Accordingly, it will be understood that dependent on the desired mode of administration the composition shall be formulated for a systemic or topical application. For example, depending on the nature and the mode of action, the composition may be administered by intra-muscular, subcutaneous, oral, intra-articular or intravenous administration. The composition can, in an aspect, be formulated for a bolus administration or can be made for continuous applications. In an aspect, the composition of the invention is an injection solution. Typically, such a injection solution is manufactured for parenteral and, in particular, intra-dermal, intra-muscular, intra- or peri-articular or intra-venously.

The first and second solution of the composition according to the invention can be mixed together and be provided as a mixed composition or they can be provided separately. In the latter case, it is envisaged according to the invention that at the site of action in the body of a subject to be treated by the composition, the said solutions form a mixture. The composition of the invention may, in an aspect, be obtained by mixing the first and the second solution in a volume ratio of about 1:1.

The term "first solution" as used herein refers to solution comprising preparations with botanical, mineral and animal-derived ingredients as well as a suitable diluent. Preparations with botanical ingredients are *Aconitum napellus, Arnica montana, radix, Bellis perennis, Belladonna, Calendula officinalis, Chamomilla, Echinacea, Echinacea purpurea, Hamamelis virginiana, Hypericum perforatum, Millefolium,* and *Symphytum officinale*. Preparations with mineral ingredients are Mercuris solubilis and *Hepar* sulphuris calcareum. The latter preparation may also be obtained from an animal, e.g., from oyster shells. Typically, said preparations are applied in the first solution of the composition in potencies according to the homeopathic pharmacopeia as follows: *Aconitum napellus* 2×, *Arnica montana, radix* 2×, *Bellis perennis* 2×, *Belladonna* 2×, *Calendula officinalis* 2×, *Chamomilla* 3×, *Echinacea* 2×, *Echinacea purpurea* 2×, *Hamamelis virginiana* 1×, *Hepar sulfuris calcareum* 6×, *Hypericum perforatum* 2×, *Mercuris solubilis* 6×, *Millefolium* 3×, and *Symphytum officinale* 6×. The aforementioned potencies of the preparations can be obtained by decimal dilutions ("D dilutions") from mother tinctures of the preparations. A "2×" potency, e.g., refers to a 1:10 dilution of the mother tincture followed by a subsequent 1:10 dilution from the first dilution. The mother tinctures for the preparations can be obtained by well known methods as described in the homeopathic pharmacopeias HAB, HPUS or Ph Eur. Moreover, the preparations in the indicated potencies are, typically, present in the first solution of the composition in an amount per 2.2 ml of about: *Aconitum napellus* 1.32 μl, *Arnica montana, radix* 2.2 μl, *Bellis perennis* 1.1 *Belladonna* 2.2 *Calendula officinalis* 2.2 μl, *Chamomilla* 2.2 μl, *Echinacea* 0.55 *Echinacea purpurea* 0.55 μl, *Hamamelis virginiana* 0.22 *Hepar sulfuris calcareum* 2.2 *Hypericum perforatum* 0.66 μl, Mercuris solubilis 1.1 μl, *Millefolium* 2.2 μl, and *Symphytum officinale* 2.2 μl. In an aspect, the said first solution referred to herein is the commercially available drug composition Trameel® (Heel Biologische Arzneimittel GmbH, Germany or Heel Inc., US). In an aspect, Traumeel® is provided in a 2.2 ml ampule.

The term "second solution" as used herein refers to solution comprising preparations with botanical, mineral and animal-derived ingredients as well as a suitable diluent. Preparations with botanical ingredients are *Arnica montana, radix, Dulcamara, Rhus toxicodendron, Sanguinaria Canadensis,* and *Symphytum officinale*. Preparations with mineral ingredients are sulphur, a-Lipoicum acidum, Coenzyme A, *Nadidum,* and *Natrum oxalaceticum*.

Typically, the second solution comprises *Arnica montana, radix, Dulcamara, Rhus toxicodendron, Sanguinaria Canadensis,* and Sulphur. In an aspect, said preparations are applied in the second solution of the composition in potencies according to the homeopathic pharmacopeia as follows: *Arnica montana, radix* 4×, *Dulcamara* 4×, *Rhus toxicodendron* 4×, *Sanguinaria Canadensis* 4×, and Sulphur 10×. Typically, the preparations are present in the second solution of the composition in an amount per 2 g of about: *Arnica montana, radix* 2 mg, *Dulcamara* 1 mg, *Rhus toxicodendron* 10 mg, *Sanguinaria Canadensis* 1 mg, and Sulphur 3 mg.

Moreover, the second solution may comprise a-Lipoicum acidum, *Arnica montana, radix, Cartilago suis,* Coenzyme A, *Dulcamara, Embryo totalis suis. Funiculus umbilicalis suis, Nadidum, Natrum oxalaceticum, Placenta suis, Rhus toxicodendron, Sanguinaria Canadensis,* Sulphur, *Symphytum officinale*. Typically, said preparations are applied in the second solution of the composition in potencies according to the homeopathic pharmacopeia as follows: a-Lipoicum acidum 8×, Arnica montana, radix 4×, Cartilago suis 6×, Coenzyme A 8×, Dulcamara 3×, Embryo totalis suis 6×, Funiculus umbilicalis suis 6×, Nadidum 8×, Natrum oxalaceticum 8×, Placenta suis 6×, Rhus toxicodendron 2×, Sanguinaria canadensis 4×, Sulphur 6×, Symphytum officinale 6×. The aforementioned potencies of the preparations can be obtained by decimal dilutions ("D dilutions") from mother tinctures of the preparations. A "2×" potency, e.g., refers to a 1:10 dilution of the mother tincture followed by a subsequent 1:10 dilution from the first dilution. The mother tinctures for the preparations can be obtained by well known methods as described in the homeopathic pharmacopeias HAB, HPUS or Ph Eur. Moreover, the preparations in the indicated potencies are, typically, present in the second solution of the composition in an amount per 2.0 ml of about: a-Lipoicum acidum 2.0 µl, Arnica montana, radix 200.0 Cartilago suis 2.0 µl, Coenzyme A 2.0 Dulcamara 10.0 µl, Embryo totalis suis 2.0 µl, Funiculus umbilicalis suis 2.0 µl, Nadidum 2.0 µl, Natrum oxalaceticum 2.0 µl, Placenta suis 2.0 µl, Rhus toxicodendron 10.0 µl, Sanguinaria canadensis 3.0 µl, Sulphur 3.6 µl, Symphytum officinale 10.0 In an aspect, the said second solution referred to herein is the commercially available drug composition Zeel® (Heel Biologische Arzneimittel GmbH, Germany or Heel Inc., US). In an aspect. Zeel® is provided in a 2.0 ml ampule.

For manufacturing the composition of the invention, the first and the second solution may, in an aspect be produced according to the homeopathic pharmacopeia and mixed together under GMP conditions. Dosage recommendations shall be indicated in the prescribers or users instructions in order to anticipate dose adjustments depending on the considered recipient.

The term "about" as used herein refers in connection with values refers to the precise value or to variations of the precise value of +/−20%, +/−15%, +/−10%, +/−5%, +1-3%, +/−2% or +/−1%.

Advantageously, the preparations comprised in the first and the second solution shall cooperate synergistically to improve inflammatory and/or degenerative conditions of the musculoskeletal system. Without being bound by theory, the preparations comprised in the first solution may accelerate tissue repair and wound healing, while the preparations comprised in the second solution may preserve cartilage structure and function.

The definitions and explanations of the terms made above apply mutatis mutandis for all following aspects and embodiments of the invention except if specified otherwise.

The present invention further relates to a method of treating and/or preventing the progression of a disease comprising administering to a subject in need of a treatment a therapeutically effective amount of the composition of the invention.

In the aforementioned method, the composition is administered in an aspect as a pre-mixed composition comprising the first and the second solution.

The term "treating" as used herein refers to any improvement of the disease or disorder that occurs in a treated subject compared to an untreated subject. Such an improvement can be a prevention of a worsening or progression of the said disease or disorder. Moreover, such an improvement may also be an amelioration or cure of the disease or disorder or its accompanying symptoms. It will be understood that a treatment may not be successful for 100% of the subjects to be treated. The term, however, requires that the treatment is successful for a statistically significant portion of the subjects (e.g. a cohort in a clinical study). Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.05, 0.01, 0.005, or 0.0001.

The term "preventing the progression of a disease" as used herein refers to avoiding or slowing down the worsening of the disease or disorder as used herein or its accompanying syndromes. It will be understood that the said prevention shall occur in accordance with the present invention within a certain time window in the future. Said time window shall, preferably, start upon administration of a compound in the sense of the invention and lasts for at least 1 week, at least 2 weeks, at least 3 weeks or at least 1 month or even more. It will be understood that said prevention may not be successful for 100% of the subjects to be treated for the prevention. The term, however, requires that the prevention is successful for a statistically significant portion of the subjects (e.g. a cohort in a cohort study). Whether a portion is statistically significant can be determined without further ado by the person skilled in the art using various well known statistic evaluation tools discussed also elsewhere herein in detail.

The term "disease" as used herein refers to any medical condition which can be treated or prevented as specified herein above by administering the composition of the invention. In an aspect, said disease is an inflammatory or degenerative condition of the musculoskeletal system. Typically, said inflammatory or degenerative condition of the musculoskeletal system is a disease or condition selected from the group consisting of: arthrosis, osteoarthritis, rheumatic joint disease, joint stiffness, pain in connection with muscles, joints and surrounding tissues or skeleton, and swelling in connection with the joints, and surrounding tissues and muscles The symptoms of said diseases and conditions are well known in the art and described in standard textbooks of medicine such as Merck manual or Kelleys textbook on Rheumatology.

The term "subject" as used herein refers to a mammal, such as farming animals including horses, pigs, cows, or sheep, or primates and, in an aspect, to a human. Typically, said subject will be in need of a treatment or prevention of a disease as specified above. Thus, in an aspect, the said subject shall suffer from or be at risk for developing the said disease. In an aspect, the said subject suffers from osteoarthritis and, in yet an aspect, osteoarthritis as defined in the accompanying Examples, below.

Administering the composition can be achieved by various modes depending on the envisaged disease to be treated. Typically, the composition is administered parenteral and, in particular, intra-dermal, intra-muscular, intra- or peri-articular or intra-venously.

A "therapeutically effective amount" which shall be administered in the method of the invention can be determined by the clinician without further ado. In an aspect, said therapeutically effective amount refers to an amount of the composition of the present invention which prevents, ameliorates or treats at least the symptoms accompanying a disease referred to in this specification. The dosage regimen will be determined by the attending physician and other clinical factors. As is well known in the medical arts, dosages for any one patient depends upon many factors, including the patient's age, the particular compound to be administered, time and route of administration, general health, and other drugs being administered concurrently. Typical dosages and dosage regimens which are envisaged by the present invention are described in the accompanying Examples, below. Progress can be monitored by periodic assessment. The composition referred to herein may be administered at least once in order to treat or ameliorate or prevent a disease recited in this specification. However, the said composition, in an aspect, may be administered more than one time.

The present invention further relates to a kit comprising a first composition and a second composition, said first solution comprising preparations of *Aconitum napellus, Arnica montana, radix, Bellis perennis, Belladonna, Calendula officinalis, Chamomilla, Echinacea, Echinacea purpurea, Hamamelis virginiana, Hepar sulfuris calcareum, Hypericum perforatum, Mercuris solubilis, Millefolium*, and *Symphytum officinale*, and said second solution comprising preparations of *Arnica montana, radix, Dulcamara, Rhus toxicodendron, Sanguinaria Canadensis*, and Sulphur.

The term "kit" as referred to herein refers to a collection of components which are packaged together in a single vial or in individual vials. In the case of the kit of the present invention, the first and the second solution may be provided, in an aspect, in separate vials, i.e. one vial for the first and another vial for the second solution. Alternatively, the first and the second solution may be comprised in a single vial which allows for a physical separation of the solutions. Usually such a physical separation can be overcome by applying physical forces, e.g., prior to administering the solutions such that the composition according to the invention can be generated in the vial. Typically, the kit may comprise additional components such as supply devices for administration of the solutions or mixing of the solutions. Moreover, there might be instructions provided in the kit for using it, in an aspect, in accordance with the method of the invention.

In an aspect said preparations are applied in the first solution in potencies according to the homeopathic pharmacopeia as follows: *Aconitum napellus* 2×. *Arnica montana, radix* 2×, *Bellis perennis* 2×. *Belladonna* 2×, *Calendula officinalis* 2×, *Chamomilla* 3×, *Echinacea* 2×, *Echinacea purpurea* 2×, *Hamamelis virginiana* 1×, *Hepar sulfuris calcareum* 6×, *Hypericum perforatum* 2×, *Mercuris solubilis* 6×, *Millefolium* 3×, and *Symphytum officinale* 6×. Typically, the preparations are present in the indicated potencies in the first solution in an amount per 2.2 ml of about: *Aconitum napellus* 1.32 µl, *Arnica montana, radix* 2.2 µl, *Bellis perennis* 1.1 µl. *Belladonna* 2.2 µl, *Calendula officinalis* 2.2 µl, *Chamomilla* 2.2 µl, *Echinacea* 0.55 µl, *Echinacea purpurea* 0.55 *Hamamelis virginiana* 0.22 µl, *Hepar sulfuris calcareum* 2.2 µl, *Hypericum perforatum* 0.66 µl, Mercuris solubilis 1.1 µl, *Millefolium* 2.2 and *Symphytum officinale* 2.2 µl.

In an aspect, said preparations are applied in the second solution of the composition in potencies according to the homeopathic pharmacopeia as follows: *Arnica montana, radix* 4×, *Dulcamara* 4×, *Rhus toxicodendron* 4×, *Sanguinaria Canadensis* 4×, and Sulphur 10×. In another aspect, the preparations are present in the second solution of the composition in an amount per 2 g of about: *Arnica montana, radix* 2 mg, *Dulcamara* 1 mg, *Rhus toxicodendron* 10 mg, *Sanguinaria Canadensis* 1 mg, and Sulphur 3 mg.

In another aspect, said second solution comprises preparations of a-Lipoicum acidum, *Arnica montana, radix, Cartilago suis*, Coenzyme A, *Dulcamara, Embryo totalis suis, Funiculus umbilicalis suis, Nadidum, Natrum oxalaceticum, Placenta suis, Rhus toxicodendron, Sanguinaria Canadensis*, Sulphur, *Symphytum officinale*. In yet another aspect, said preparations are applied in the second solution in potencies according to the homeopathic pharmacopeia as follows: a-Lipoicum acidum 8×, *Arnica montana, radix* 4×, *Cartilago suis* 6×, Coenzyme A 8×, *Dulcamara* 3×, *Embryo totalis suis* 6×, *Funiculus umbilicalis suis* 6×, Nadidum 8×, *Natrum oxalaceticum* 8×, *Placenta suis* 6×, *Rhus toxicodendron* 2×, *Sanguinaria canadensis* 4×, Sulphur 6×, *Symphytum officinale* 6×. Typically, the preparations are present in the indicated potencies in the second solution in an amount per 2.0 ml of about: a-Lipoicum acidum 2.0 µl, *Arnica montana, radix* 200.0 *Cartilago suis* 2.0 Coenzyme A 2.0 µl, *Dulcamara* 10.0 µl, *Embryo totalis suis* 2.0 µl, *Funiculus umbilicalis suis* 2.0 µl, Nadidum 2.0 µl, *Natrum oxalaceticum* 2.0 µl, *Placenta suis* 2.0 µl. *Rhus toxicodendron* 10.0 µl, *Sanguinaria canadensis* 3.0 µl, Sulphur 3.6 µl, *Symphytum officinale* 10.0 µl.

The present invention further relates to a method of treating and/or preventing the progression of a disease progression comprising administering to a subject in need of a treatment a therapeutically effective amount of a first and a second solution, said first solution comprising preparations of *Aconitum napellus, Arnica montana, radix, Bellis perennis, Belladonna, Calendula officinalis, Chamomilla, Echinacea, Echinacea purpurea, Hamamelis virginiana, Hepar sulfuris calcareum, Hypericum perforatum, Mercuris solubilis, Millefolium*, and *Symphytum officinale*, and said second solution comprising preparations of *Arnica montana, radix, Dulcamara, Rhus toxicodendron, Sanguinaria Canadensis*, and Sulphur.

In the aforementioned method, the first and the second solution of the composition are administered separately such that the composition comprising the first and the second solution is formed at the site of action in the subject.

In an aspect, said preparations are applied in the first solution in potencies according to the homeopathic pharmacopeia as follows: *Aconitum napellus* 2×, *Arnica montana, radix* 2×, *Bellis perennis* 2×, *Belladonna* 2×, *Calendula officinalis* 2×, *Chamomilla* 3×, *Echinacea* 2×, *Echinacea purpurea* 2×, *Hamamelis virginiana* 1×, *Hepar sulfuris calcareum* 6×, *Hypericum perforatum* 2×, *Mercuris solubilis* 6×, *Millefolium* 3×, and *Symphytum officinale* 6×. Typically, the preparations in the indicated potencies are present in the first solution in an amount per 2.2 ml of about: *Aconitum napellus* 1.32 µl, *Arnica montana, radix* 2.2 µl, *Bellis perennis* 1.1 µl, *Belladonna* 2.2 µl, *Calendula officinalis* 2.2 µl. *Chamomilla* 2.2 µl, *Echinacea* 0.55 µl, *Echinacea purpurea* 0.55 µl, *Hamamelis virginiana* 0.22 µl, *Hepar sulfuris calcareum* 2.2 µl, *Hypericum perforatum* 0.66 µl, Mercuris solubilis 1.1 µl, *Millefolium* 2.2 µl, and *Symphytum officinale* 2.2 µl.

In an aspect, said preparations are applied in the second solution of the composition in potencies according to the homeopathic pharmacopeia as follows: *Arnica montana, radix* 4×, *Dulcamara* 4×, *Rhus toxicodendron* 4×, *Sanguinaria Canadensis* 4×, and Sulphur 10×. In another aspect, the preparations are present in the second solution of the composition in an amount per 2 g of about: *Arnica montana, radix* 2 mg, *Dulcamara* 1 mg, *Rhus toxicodendron* 10 mg, *Sanguinaria Canadensis* 1 mg, and Sulphur 3 mg.

In another aspect, said second solution comprises preparations of a-Lipoicum acidum, *Arnica montana, radix, Cartilago suis*, Coenzyme A, *Dulcamara, Embryo totalis suis, Funiculus umbilicalis suis, Nadidum, Natrum oxalaceticum, Placenta suis, Rhus toxicodendron, Sanguinaria Canadensis*, Sulphur, *Symphytum officinale*. In a further aspect, said preparations are applied in the second solution in potencies according to the homeopathic pharmacopeia as follows: a-Lipoicum acidum 8×, *Arnica montana, radix* 4×, *Cartilago suis* 6×, Coenzyme A 8×, *Dulcamara* 3×, *Embryo totalis suis* 6×, *Funiculus umbilicalis suis* 6×, Nadidum 8×, *Natrum oxalaceticum* 8×, *Placenta suis* 6×, *Rhus toxicodendron* 2×, *Sangui-*

*naria canadensis* 4×, Sulphur 6×, *Symphytum officinale* 6×. Typically, the preparations are present in the indicated potencies in the second solution in an amount per 2.0 ml of about: a-Lipoicum acidum 2.0 µl, *Arnica montana, radix* 200.0 µl, *Cartilago suis* 2.0 µl, Coenzyme A 2.0 µl, *Dulcamara* 10.0 µl, *Embryo totalis suis* 2.0 µl, *Funiculus umbilicalis suis* 2.0 µl, *Nadidum* 2.0 µl, *Natrum oxalaceticum* 2.0 µl, *Placenta suis* 2.0 µl, *Rhus toxicodendron* 10.0 *Sanguinaria canadensis* 3.0 µl, Sulphur 3.6 µL *Symphytum officinale* 10.0 µl.

All references cited throughout this specification are herewith incorporated by reference either with respect to their disclosure contents in the entirety or with respect to the specific disclosures referred to before.

EXAMPLES

The invention will now be illustrated by the following Examples. The Examples, however, must not be construed as limiting the scope of the invention in any respect.

Example

Investigation of Synergistic Action of Traumeel and Zeel in the Treatment of Osteoarthritis The study is a multi-center, double-blind, randomized, placebo-controlled, 2-armed trial. Two hundred patients (N=200) with documented diagnosis of primary osteoparthritis (OA) of one or both knees and experiencing moderate to severe pain will be randomized in a balanced 1:1 ratio to Placebo (N=100) and Traumeel®/Zeel® treatment (N=100). After screening procedures, eligible patients will enter a 7-day washout period at which time patients will discontinue all current medications taken for OA pain (including non-opioid/NSAIDs with long half-lives, e.g., piroxicam, oxaprozin). After the 7-day washout period, patients will enter a minimum 3 days Lead-In period up to maximum 10 days. At Visit 2/start of placebo Lead-In eligibility period, a diary will be provided to record their pain levels each evening using a Likert five-point numeric scale (none, mild, moderate, severe, extreme) to answer the question:

"How much knee pain have you had during the last 24 hours in your target knee? If your pain is at least moderate, call the study site to schedule your Baseline visit."

This information is only used for the purpose of properly engaging the patient to participate in the study and will be maintained separate from the clinical database. Only the 50-foot walk test that is performed at the study site will be used to determine study eligibility.

At all visits, the Western Ontario and McMaster Universities Osteoarthritis Index (WOMAC) Visual Analog Scale (VAS) version 100 mm OA questionnaire for pain, morning stiffness, and physical function will be completed. In addition, pain will be assessed immediately following a 50-foot walk test, using a 100 mm VAS. Moreover, time on the 50-foot walk test will also be measured.

The following patients will not be randomized:

Patients who fail to experience a flare during the placebo Lead-In period

Patients who document pain improvement of one (1) unit or greater (Likert Scale—this is equivalent to 25 mm or greater on VAS scale) on at least 3 continuous days during the oral placebo Lead-In period. These patients will be defined as placebo responders.

All primary and secondary endpoints will be evaluated at Baseline. The Visit 3 (Day 1, pre intra-articular injection) 50-foot walk test VAS pain score will be used as an essential inclusion criterion. Eligible patients will be randomized to receive either IA injections of a co-administered mixture of Traumeel® and Zeel® or Placebo (saline) into the target knee approximately every 7 days (Days 1, 8 and 15) over a 15-days treatment period for a total of 3 injections. Pain assessments for eligibility and other Baseline assessments will take place at every visit. All assessments will be performed pre-dose. The 15-day treatment period will be followed by a 12-week follow up period with site visits on alternate weeks and a follow up phone call to patients in between visits as follows: Day 29 (Visit 7), Day 43 (Visit 9), Day 57 (Visit 11), Day 71 (Visit 13) and Day 85 (Visit 15). The final assessments will be performed on Day 99 (Visit 17), approximately 12 weeks after the third injection. Full WOMAC assessments will be conducted during visits to the study site. When at home, at the time of the weekly phone call from the study staff, patients will document in a diary their response to WOMAC Question A1 for the last 24 hours "How much pain have you had walking on a flat surface"? (VAS 100 mm scale). They will also document the use of rescue medication. Safety and efficacy assessments will be performed.

Patients will be allowed to rescue from Day 1 through Day 99 with acetaminophen (paracetamol) 500 mg/tablet (PRN), at a maximum dose of 6 tablets or 3000 milligrams per day (mg/d) but not exceeding 4 consecutive days in a 7 day period or not more than 12,000 mg in a 7 day period. Patients will not be allowed to take acetaminophen within 24 hours prior to a clinical visit.

What is claimed is:

1. A method of treating the progression of an inflammatory or degenerative disease or condition of the musculoskeletal system, comprising administering to a subject in need of a treatment a therapeutically effective amount of a composition comprising:
   (i) a first solution comprising preparations that are extracts of *Aconitum napellus, Arnica montana radix, Bellis perennis, Belladonna, Calendula officinalis, Chamomilla, Echinacea, Echinacea purpurea, Hamamelis virginiana, Hepar sulfuris calcareum, Hypericum perforatum, Millefolium,* and *Symphytum officinale* and Mercuris solubilis, and
   (ii) a second solution comprising preparations that are extracts of *Arnica montana, radix, Dulcamara, Rhus toxicodendron,* and *Sanguinaria Canadensis,* and Sulphur.

2. The method of claim 1, wherein said inflammatory or degenerative disease or condition of the musculoskeletal system is a disease or condition selected from the group consisting of: arthrosis, osteoarthritis, rheumatic joint disease, joint stiffness, pain in connection with muscles or skeleton, and swelling in connection with muscles or skeleton.

3. The method of claim 1, wherein said composition is administered by a method selected from the group consisting of parenteral, intra-dermal, intra-muscular, intra-articular, peri-articular, and intra-venously.

4. A method of treating the progression of an inflammatory or degenerative disease or condition of the musculoskeletal system, comprising administering to a subject in need of a treatment a therapeutically effective amount of a first and a second solution, said first solution comprising preparations that are extracts of *Aconitum napellus, Arnica montana radix, Bellis perennis, Belladonna, Calendula officinalis, Chamomilla, Echinacea, Echinacea purpurea, Hamamelis virginiana, Hepar sulfuris calcareum, Hypericum perforatum, Millefolium,* and *Symphytum officinale* and Mercuris solubilis, and said second solution comprising preparations that are extracts of *Arnica montana, radix, Dulcamara, Rhus toxicodendron*, and *Sanguinaria Canadensis*, and Sulphur.

5. The method of claim 4, wherein said preparations are present in the first solution in potencies according to the homeopathic pharmacopeia as follows: *Aconitum napellus* 2×, *Arnica montana, radix* 2×, *Bellis perennis* 2×, *Belladonna* 2×, *Calendula officinalis* 2×, *Chamomilla* 3×, *Echinacea* 2×, *Echinacea purpurea* 2×, *Hamamelis virginiana* 1×, *Hepar sulfuris calcareum* 6×, *Hypericum perforatum* 2×, Mercuris solubilis 6×, *Millefolium* 3×, and *Symphytum officinale* 6×.

6. The method of claim 5, wherein the preparations are present in the first solution in an amount per 2.2 ml of about: *Aconitum napellus* 1.32 µl, *Arnica montana, radix* 2.2 µl, *Bellis perennis* 1.1 µl, *Belladonna* 2.2 µl, *Calendula officinalis* 2.2 µl, *Chamomilla* 2.2 µl, *Echinacea* 0.55 µl, *Echinacea purpurea* 0.55 µl, *Hamamelis virginiana* 0.22 µl, *Hepar sulfuris calcareum* 2.2 µl, *Hypericum perforatum* 0.66 µl, Mercuris solubilis 1.1 µl, *Millefolium* 2.2 µl, and *Symphytum officinale* 2.2 µl.

7. The method of claim 4, wherein said preparations are present in the second solution of the composition in potencies according to the homeopathic pharmacopeia as follows: *Arnica montana, radix* 4×, *Dulcamara* 4×, *Rhus toxicodendron* 4×, *Sanguinaria canadensis* 4×, and Sulphur 10×.

8. The method of claim 7, wherein the preparations are present in the second solution of the composition in an amount per 2 g of about: *Arnica montana, radix* 2 mg, *Dulcamara* 1 mg, *Rhus toxicodendron* 10 mg, *Sanguinaria canadensis* 1 mg, and Sulphur 3 mg.

9. The method of claim 4, wherein said second solution further comprises preparations of a-Lipoicum acidum, *Cartilago suis*, Coenzyme A, *Embryo totalis suis*, *Funiculus umbilicalis suis*, Nadidum, Natrum oxalaceticum, *Placenta suis*, and *Symphytum officinale*.

10. The method of claim 9, wherein said preparations are present in the second solution in potencies according to the homeopathic pharmacopeia as follows: a-Lipoicum acidum 8×, *Arnica montana, radix* 4×, *Cartilago suis* 6×, Coenzyme A 8×, *Dulcamara* 3×, *Embryo totalis suis* 6×, *Funiculus umbilicalis suis* 6×, Nadidum 8×, Natrum oxalaceticum 8×, *Placenta suis* 6×, *Rhus toxicodendron* 2×, *Sanguinaria canadensis* 4×, Sulphur 6×, *Symphytum officinale* 6×.

11. The method of claim 10, wherein the preparations are present in the second solution in an amount per 2.0 ml of about: a-Lipoicum acidum 2.0 µl, *Arnica montana, radix* 200.0 µl, *Cartilago suis* 2.0 µl, Coenzyme A 2.0 µl, *Dulcamara* 10.0 µl, *Embryo totalis suis* 2.0 µl, *Funiculus umbilicalis suis* 2.0 µl, *Nadidum* 2.0 µl, *Natrum oxalaceticum* 2.0 µl, *Placenta suis* 2.0 µl, *Rhus toxicodendron* 10.0 µl, *Sanguinaria canadensis* 3.0 µl, Sulphur 3.6 µl, and *Symphytum officinale* 10.0 µl.

12. The method of claim 4, wherein said inflammatory or degenerative disease or condition of the musculoskeletal system is a disease or condition selected from the group consisting of: arthrosis, osteoarthritis, rheumatic joint disease, joint stiffness, pain in connection with muscles or skeleton, and swelling in connection with muscles or skeleton.

13. The method of claim 4, wherein said compositions are administered by a method selected from the group consisting of parenteral, intra-dermal, intra-muscular, intra-articular, pert-articular, and intra-venously.

14. The method of claim 2, wherein said inflammatory or degenerative disease or condition of the musculoskeletal system is arthrosis.

15. The method of claim 2, wherein said inflammatory or degenerative disease or condition of the musculoskeletal system is osteoarthritis.

16. The method of claim 2, wherein said inflammatory or degenerative disease or condition of the musculoskeletal system is rheumatic joint disease.

17. The method of claim 2, wherein said inflammatory or degenerative disease or condition of the musculoskeletal system is joint stiffness.

18. The method of claim 12, wherein said inflammatory or degenerative disease or condition of the musculoskeletal system is arthrosis.

19. The method of claim 12, wherein said inflammatory or degenerative disease or condition of the musculoskeletal system is osteoarthritis.

20. The method of claim 12, wherein said inflammatory or degenerative disease or condition of the musculoskeletal system is rheumatic joint disease.

21. The method of claim 12, wherein said inflammatory or degenerative disease or condition of the musculoskeletal system is joint stiffness.

* * * * *